(12) United States Patent
Hamprecht et al.

(10) Patent No.: US 6,191,280 B1
(45) Date of Patent: Feb. 20, 2001

(54) METHOD FOR PRODUCING SUBSTITUTED THIOPYRIDINES

(75) Inventors: Gerhard Hamprecht, Weinheim; Markus Menges, Bensheim; Olaf Menke, Altleiningen; Robert Reinhard, Ludwigshafen; Peter Schäfer, Ottersheim; Cyrill Zagar, Ludwigshafen, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/423,961

(22) PCT Filed: May 15, 1998

(86) PCT No.: PCT/EP98/02879

§ 371 Date: Nov. 17, 1999

§ 102(e) Date: Nov. 17, 1999

(87) PCT Pub. No.: WO98/54139

PCT Pub. Date: Dec. 3, 1998

(30) Foreign Application Priority Data

May 30, 1997 (DE) ............................... 197 22 661

(51) Int. Cl.[7] ...................... C07D 213/32; C07D 213/44; C07D 213/52
(52) U.S. Cl. .................. 546/294; 546/291; 546/339; 546/286; 546/313
(58) Field of Search .................................. 546/286, 290, 546/313, 339, 291, 294

(56) References Cited

U.S. PATENT DOCUMENTS

| 3,725,421 | * | 4/1973 | Domenico | 546/291 |
| 3,894,035 | * | 7/1975 | Domenico | 546/291 |
| 4,946,854 |   | 8/1990 | Maienfisch et al. . | |
| 5,783,522 |   | 7/1998 | Schaefer et al. . | |
| 6,022,884 | * | 2/2000 | Mantlo et al. | 514/352 |

FOREIGN PATENT DOCUMENTS

| 43 23 916 |   | 1/1995 | (DE) . |
| 196 36 995 |   | 3/1998 | (DE) . |
| 0036638 | * | 3/1981 | (EP) . |
| 320 448 |   | 6/1989 | (EP) . |
| 2 223 017 |   | 3/1990 | (GB) . |
| 98/11072 |   | 3/1998 | (WO) . |

OTHER PUBLICATIONS

J. Chem.Soc., Perkin Trans., Part I (1980) 648–656, Bratt et al.
Bull. Soc., Chim. Belg. 101, 297–302 (1992).
J.Chem. Soc. 1952, 2057–2062.
Liebigs Ann. 1995, 591/592 (with translation).

* cited by examiner

Primary Examiner—Alan L. Rotman
Assistant Examiner—Rita Desai
(74) Attorney, Agent, or Firm—Keil & Weinkauf

(57) ABSTRACT

A process for preparing thiopyridines of the formula I

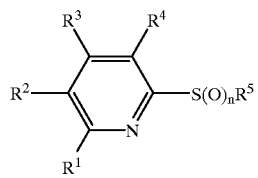

I where the substituents are as defined in the description.

4 Claims, No Drawings

METHOD FOR PRODUCING SUBSTITUTED THIOPYRIDINES

CROSS-REFERENCE

This application is a 371 of PCT/EP98/02879 filed may 15, 1998.

The present invention relate to a process for preparing thiopyridines of the formula I

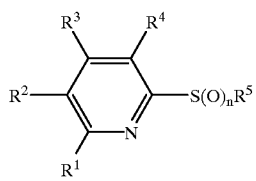

in which
n is 0, 1 or 2
$R^1, R^2, R^3$ and $R^4$ are identical or different and each is hydrogen, halogen, nitro, cyano; $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_3$–$C_6$-alkynyloxy, $C_1$–$C_6$-alkylthio, $C_2$–$C_6$-alkenylthio, $C_3$–$C_6$-alkynylthio, $C_1$–$C_6$-alkylsulfinyl, $C_2$–$C_6$-alkenylsulfinyl, $C_3$–$C_6$-alkynylsulfinyl, $C_1$–$C_6$-alkylsulfonyl, $C_2$–$C_6$-alkenylsulfonyl, $C_3$–$C_6$-alkynylsulfonyl, it being possible for the alkyl, alkenyl and alkynyl moieties of these groups to carry up to 6 halogen atoms; a $C_1$–$C_4$-alkylenephenyl, phenyl, phenoxy or naphthyl radical without substitution in the phenyl or naphthyl moiety or with substitution by halogen, $C_1$–$C_3$-alkyl, $C_1$–$C_3$-alkoxy, trifluoromethyl, cyano or nitro; $CO_2R^6$, $CONR^7R^8$, $SO_2NR^7R^8$ or $COR^6$; furthermore, if located in adjacent positions on the pyridine ring, they together form a 5- or 6-membered aromatic or aliphatic ring which may contain one or more hetero atoms or may be substituted by halogen, trifluoromethyl, methyl or methoxy;
$R^5$ is a $C_1$–$C_{10}$-alkyl, $C_2$–$C_{10}$-alkenyl or $C_2$–$C_{10}$-alkynyl radical without substitution or with substitution by halogen, $C_1$–$C_4$-alkoxy, $C_1$–$C_4$-alkoxycarbonyl, di-($C_1$–$C_4$-alkyl)aminocarbonyl, cyano or nitro, a $C_3$–$C_8$-cycloalkyl radical, a $C_1$–$C_4$-alkylenephenyl, phenyl or naphthyl radical without substitution in the phenyl or naphthyl moiety or with substitution by halogen, $C_1$–$C_3$-alkyl, $C_1$–$C_3$-alkoxy, trifluoromethyl, cyano or nitro,
$R^6$, $R^7$ and $R^8$ are identical or different and each is hydrogen; $C_1$–$C_6$-alkyl, $C_3$–$C_6$-cycloalkyl, $C_2$–$C_6$-alkenyl, $C_3$–$C_6$-alkynyl, it being possible for these groups to carry up to 6 halogen atoms; a phenyl or $C_1$–$C_4$-alkylenephenyl radical without substitution in the phenyl moiety or with substitution by halogen, $C_1$–$C_3$-alkyl, $C_1$–$C_3$-alkoxy, trifluoromethyl, cyano or nitro.

The thiopyridines I are important intermediates for preparing crop protection agents having herbicidal activity as disclosed in WO-A-95/02580.

In the literature, the synthesis of pyridine thioethers starting from thiols and halopyridines is usually carried out in the presence of bases (J. Chem. Soc., Perkin Trans., Part I (1980) 648; Bull. Soc. Chim. Belg. 101 (1992) 297).

In GB 2 223 017, the sodium salt of the thio component is reacted with the halopyridine in the presence of copper bronze, affording the corresponding pyridine thioether in 31% yield.

Finally, EP 320448 discloses the reaction of a 2-halopyridine with anilines without the addition of a base to give the corresponding 2-arylaminopyridine in a yield of 11 or 37%. In the same publication, it is furthermore mentioned that, besides anilines, it is also possible to use thiophenols. However, EP-A 320 448 does not give any concrete working example describing the reaction of a 2-halopyridine with a thiophenol.

It is an object of the present invention to provide a simple and economical process for preparing thiopyridine derivatives which in turn are suitable as coupling components for preparing substituted phenylpyridines as described in WO-A-95/02580.

We have found that this object is achieved by the process for preparing thiopyridines of the formula I defined at the outset

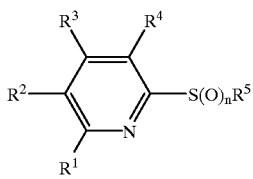

which comprises reacting substituted 2-halopyridines of the formula II

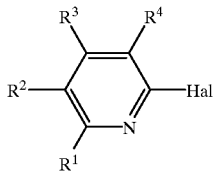

in which $R^1$, $R^2$, $R^3$ and $R^4$ are each as defined above and Hal is fluorine, chlorine or bromine, in a first step with a thio compound of the formula III

HS—$R^5$                                                            III in which $R^5$ is as defined above, in the presence of a copper catalyst to give initially a pyridine thioether of the formula Ia and then oxidizing this stepwise to give the sulfoxide Ib or sulfone Ic

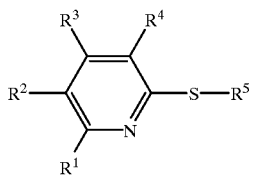

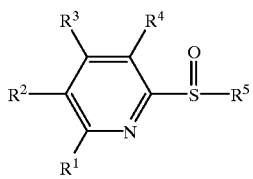

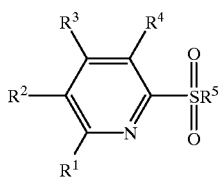

The process according to the invention affords the pyridine thioethers of the formula Ia in a surprisingly high yield. The pyridine thioethers Ia formed are so pure that they can generally be oxidized without intermediate isolation with oxidizing agents to give the sulfoxides Ib and Ic.

Hydrogen peroxide in acetic acid or acetic acid/trifluoroacetic acid mixtures has been found to be particularly advantageous for oxidizing the pyridine thioethers Ia stepwise to the sulfoxides Ib and the sulfones Ic. Hypochlorous acid or its alkali metal salt has been found to be particularly suitable for the direct oxidation of pyridine thioethers Ia to sulfones Ic. The thiopyridines I are particularly preferably obtained by initially reacting substituted 2-halopyridines of the formula II

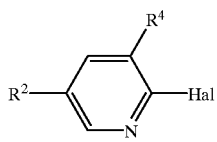

in which $R^2$, $R^4$ and Hal are each as defined above, in a first step with a thio compound of the formula III

   III in which $R^5$ is as defined above, in the presence of from 0.001 to 1 mol % of a copper catalyst to give a pyridine thioether of the formula Ia which is then oxidized stepwise to the sulfoxide Ib

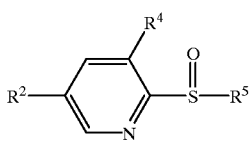

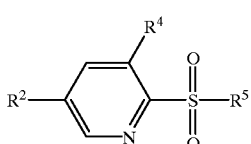

or sulfone Ic.

Compounds which are particularly preferred for use as compound II are 2,3,5-trichloropyridine, 5-chloro-2,3-difluoropyridine, 2,3-dichloro-5-difluoromethylpyridine, 2,3-dichloro-5-(3,3,3-trifluoropropyl)pyridine, 2,3-dichloro-5-trifluoromethylpyridine and 2,3-dichloro-5-pentafluoroethylpyridine.

The preparation of the compounds I is exemplified by the reaction starting from 2,3-dichloro-5-trifluoromethylpyridine and thiophenol as nucleophile, using hydrogen peroxide as oxidizing agent, illustrated in the scheme that follows.

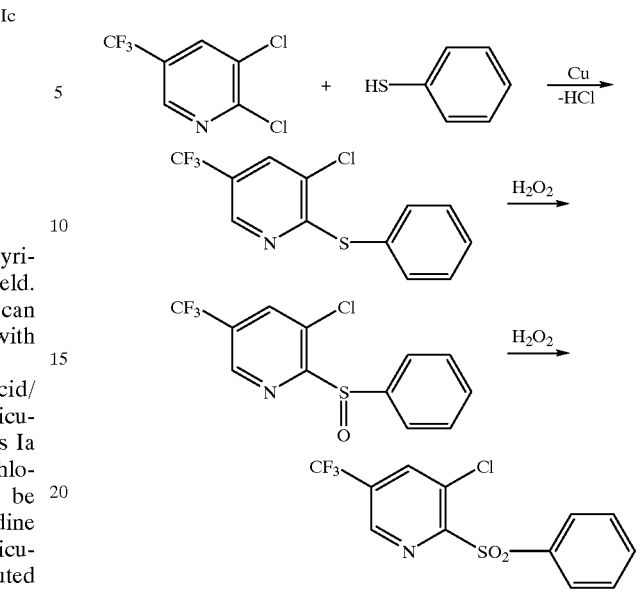

It is also possible to use the oxidizing agents mentioned below instead of hydrogen in a similar manner.

Preferred embodiments of the process are specified below:

The reaction of the 2-halopyridines II with a thiol III is advantageously carried out in the presence of a solvent at 80–250° C., preferably 120–200° C., particularly preferably 140–180° C. Solvents that are used for these reactions—depending on the temperature range—are hydrocarbons such as toluene and xylene, chlorinated hydrocarbons such as 1,2-dichloroethane, 1,1,2,2-tetrachloroethane, chlorobenzene, 1,2-, 1,3- or 1,4-dichlorobenzene, ethers such as 1,4-dioxane or anisole, glycol ethers such as glycol dimethyl ether, glycol diethyl ether or diethylene glycol dimethyl ether, esters such as ethyl acetate, propyl acetate, methyl isobutyrate or isobutyl acetate, carboxamides such as DMF or N-methylpyrrolidone, nitrated hydrocarbons such as nitrobenzene, ureas such as tetraethylurea, tetrabutylurea, dimethylethyleneurea and dimethylpropyleneurea, sulfoxides such as dimethyl sulfoxide, sulfones such as dimethyl sulfone, diethyl sulfone and tetramethylene sulfone, nitriles such as acetonitrile, propionitrile, butyronitrile or isobutyronitrile; water, or else mixtures of individual solvents.

The reaction is particularly preferably carried out in the melt without the use of a solvent.

The molar ratios in which the starting materials are reacted with each other are generally 0.9–1.4, preferably 0.95–1.1, particularly preferably 0.98–1.04, for the ratio of thiol to 2-halopyridine II. The concentration of the starting materials in the solvent is 0.1–5 mol/l, preferably 0.2–2 mol/l.

Suitable catalysts are copper oxide, salts such as copper (II) chloride, copper sulfate, copper nitrate, copper acetate and copper carbonate. Particular preference is given to using finely dispersed metallic copper, for example copper powder or copper bronze. The molar amount of catalyst, based on the 2-halopyridine II, is 0.001–10, preferably 0.001–1 mol % and particularly preferably 0.001 to 0.1 mol %.

The reaction is preferably carried out under acidic conditions by flushing the hydrogen halide that is eliminated during the reaction out of the reaction mixture by means of an inert gas, for example nitrogen, or by letting it escape into a gas washer under autogenous pressure.

Advantageously, the 2-halopyridine II is added over a period of 10 to 60 min to a mixture of the thiol III and the catalyst at 20–80° C., and the mixture is then stirred for another 0.5 to 12 hours, preferably 1 to 8 hours, at 140–180° C. to allow the reaction to go to completion.

However, it is also possible to add the thiol III to a mixture of 2-halopyridine II and catalyst and then to complete the reaction as described above.

In the case of low-boiling 2-halopyridines II or thiols III, the reaction can also be carried out in an autoclave.

If only one of the two starting materials has a low boiling point, the higher-boiling component can be initially charged together with the catalyst, and the lower-boiling component can be added, or passed in as gas, directly at the reaction temperature of preferably 120–200° C., particularly preferably 140–180° C., at the rate of its consumption.

Finally, the reaction can also be carried out in an aqueous two-phase system, preferably in the presence of phase transfer catalysts such as quaternary ammonium or phosphonium salts. Suitable conditions for the two-phase reaction are described in EP-A-556 737.

The reaction can be carried out under atmospheric or superatmospheric pressure, continuously or batchwise.

The oxidation of the pyridine thioethers of the formula Ia to the sulfoxides Ib and sulfones Ic can preferably be carried out with hydrogen peroxide, the sulfoxides Ib resulting with approximately equivalent amounts of oxidant, and in the sulfones Ic with approximately double the molar amounts.

Examples of solvents which can be used are water, acetonitrile, carboxylic acids such as acetic acid, trifluoroacetic acid, propionic acid, alcohols such as methanol, ethanol, isopropanol, tert-butanol and chlorinated hydrocarbons such as methylene chloride, 1,1,2,2-tetrachloroethane, or ketones such as acetone or methyl ethyl ketone. Water, methanol, acetic acid and trifluoroacetic acid are particularly preferred.

In a particularly preferred variant, the reaction can also be catalyzed by adding relatively strong acids such as trifluoroacetic acid or perchloric acid. However, suitable catalysts are also metal compounds, eg. transition metal oxides such as vanadium pentoxide, sodium tungstate, potassium dichromate, iron oxide tungstate, sodium tungstate/molybdic acid, osmic acid, titanium trichloride, selenium dioxide, phenylselenenic acid, vanadyl 2,4-pentanedionate.

The catalysts are generally employed in an amount of from 0.5 to 10%, but it is also possible to employ stoichiometric amounts because the inorganic catalysts can easily be filtered off and recovered.

Another preferred oxidizing agent is peracetic acid or hydrogen peroxide/acetic anhydride, possibly also the peracetic acid which is present in equilibrium in a hydrogen peroxide/acetic acid mixture.

Another preferred oxidizing agent is pertrifluoroacetic acid or the hydrogen peroxide/trifluoroacetic acid mixture or else the hydrogen peroxide/trifluoroacetic anhydride mixture.

Oxidation with hydrogen peroxide in glacial acetic acid is generally very selective, but frequently slow. The reaction time can generally be reduced by adding trifluoroacetic acid. The oxidation with hydrogen peroxide in pure trifluoroacetic acid frequently leads to the formation of the corresponding N-oxides, as also described in Chimia 29 (1975), 466. A rapid and selective oxidation of the pyridine thioethers Ia to the corresponding sulfoxides Ib and sulfones Ic is possible using solutions of hydrogen peroxide in mixtures of acetic acid and trifluoroacetic acid in the ratio of 10:1 to 1:1, in particular 6:1 to 4:1, by volume. Therefore particular preference is given to using these mixtures as solvent.

It is possible furthermore to use as solvent petroleum ether, the abovementioned solvents and the abovementioned catalysts.

Besides peracetic acid and pertrifluoroacetic acid, it is also possible to employ perbenzoic acid, monoperphthalic acid or 3-chloroperbenzoic acid, expediently in chlorinated hydrocarbons such as methylene chloride or 1,2-dichloroethane.

Also very suitable for oxidizing the thiols to sulfoxides or sulfones are chlorine and bromine. Favorable solvents are water, acetonitrile, dioxane, two-phase systems such as aqueous potassium bicarbonate solution/dichloromethane, and, in the case of pyridine alkyl thioethers, also acetic acid.

It is furthermore possible to employ as source of active halogen tert-butyl hypochlorite, hypochlorous and hypobromous acids, their salts, also N-halo compounds such as N-bromo- and N-chlorosuccinimide or else sulfuryl chloride.

Also favorable for the oxidation are dinitrogen tetroxide, eg. in the technically simple variant with air/nitrogen dioxide or trioxide and, for example, osmium(VIII) oxide as catalyst. The oxidation can also be carried out directly with nitric acid, in which case suitable additional solvents are acetic anhydride and acetic acid, and suitable catalysts are copper(I) and (II) bromide and chloride.

Also suitable for the oxidation is photosensitized oxygen transfer, in which case recommended photosensitizers are chlorophyll, protoporphyrin, Rose Bengal or Methylene Blue. Suitable inert solvents are hydrocarbons such as pentane, hexane, heptane, cyclohexane, chlorinated hydrocarbons such as methylene chloride, 1,2-dichloroethane, 1,1,2,2-tetrachloroethane, alcohols such as methanol, ethanol, n-propanol or isopropanol, ketones such as acetone, methyl ethyl ketone, polar aprotic solvents such as acetonitrile, propionitrile or aromatic hydrocarbons such as benzene, toluene, chlorobenzene or xylene. In place of oxygen, it is also possible to use ozone in the abovementioned solvents, plus ether, 1,4-dioxane or THF.

Besides photosensitization, catalysts can also be recommended for oxidation with oxygen, eg. oxides and sulfides of nickel, copper, aluminum, tungsten, chromium, vanadium, ruthenium, titanium, manganese, molybdenum, magnesium and iron.

Either pyridine sulfoxides Ib or their pyridine sulfones Ic are obtained depending on the stoichiometry of the oxidizing agents used. The molar ratios in which the starting materials are reacted with each other are generally 0.9–1.8, preferably 1.05–1.3, for the ratio of pyridine thioether Ia to oxidizing agent in the case of oxidation to pyridine sulfoxide and generally 1.9–3.5, preferably 2.05–2.9, in the case of oxidation to pyridine sulfone.

The concentration of the starting materials in the solvent is generally 0.1–5 mol/l, preferably 0.2–2 mol/l.

It is advantageous to introduce the pyridine thioether or the pyridine sulfoxide, if appropriate with one of the abovementioned catalysts, into one of the abovementioned solvents and then to add the oxidizing agent over the course of 0.25–20 hours with stirring. The addition and reaction temperatures depend on the optimum efficiency of the oxidizing agents in question and the avoidance of side reactions. If photosensitized oxygen is used, the reaction is generally carried out at −20 to 80° C., but in the case of metal catalysis, the reaction is generally carried out at 50 to 140° C., and if ozone is used, the reaction is generally carried out at −78 to 60° C. Owing to the limited solubility of the oxygen derivatives, they have to be passed continuously over a prolonged period of time (up to 20 hours) into the reaction mixture until the oxidation has ended at the sulfoxide or sulfone stage. If air/nitrogen dioxide or trioxide are used, the reaction is preferably carried out at 15–150° C. over a period of 1–15 hours. Liquid or readily soluble oxidizing agents such as hydrogen peroxide, the peracetic acid and pertrifluoroacetic acid which are formed together with acetic anhydride or in equilibrium with acetic acid and trifluoroacetic acid, respectively, hypochlorous or hypobromous acid, tert-butyl hypochlorite, chlorine or bromine, N-chlorosuccinimide or N-bromosuccinimide or nitric acid can be added over shorter periods of time of, depending on the exothermic character of the reaction, 0.25–6 hours to the reaction mixture of the pyridine thioether or sulfoxide in order to end the reaction after a further 1–60 ours. Moreover, preference is given to adding the liquid or dissolved oxidizing agent in portions. If hydrogen peroxide and peracetic acid or pertrifluoroacetic acid are used, the reaction is generally carried out at 0–90° C., if tert-butyl hypochlorite is used, the reaction is generally carried out at −78 to 30° C., if halo compounds are used, the reaction is generally carried out at 0–30° C., and if nitric acid is used, the reaction is generally carried out at 20 to 140° C. If chlorine or bromine is used, a reaction temperature of 0–40° C. is recommended.

The oxidations can be carried out under atmospheric or superatmospheric pressure, continuously or batchwise.

Advantageously, the multi-step reaction can also be carried out as a one-pot reaction, by reacting the pyridine thioethers Ia which are obtained in the first step of the synthesis on reaction of the 2-halopyridines II with the thiols III without isolation and purification directly to give the sulfoxides Ib or the sulfones Ic. Thus, if appropriate, the reaction product Ia is allowed to cool to 90–20° C., a solvent, for example trifluoroacetic acid, preferably acetic acid and/or water, is added, if appropriate, and the oxidizing agent is then added at the rate of its consumption. Preferred oxidizing agents for the one-pot method are hydrogen peroxide and especially sodium hypochlorite.

For work-up, the end products I are taken up in a water-immiscible solvent, acidic impurities and/or oxidizing agents are extracted using dilute alkali or water, the solution is dried and the solvent is removed under reduced pressure.

Using this process, it is possible to obtain, preferably, the novel substituted thiopyridines of the formula I'

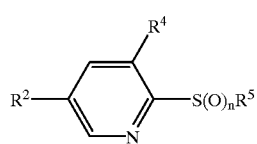

in which
n is 1 or 2;
$R^2$ is chlorine, $C_1$–$C_3$-fluoroalkyl, cyano or methylsulfonyl;
$R^4$ is fluorine or trifluoromethyl;
$R^5$ is a $C_1$–$C_{10}$-alkyl, $C_2$–$C_{10}$-alkenyl or $C_2$–$C_{10}$-alkynyl radical without substitution or with substitution by halogen, $C_1$–$C_4$-alkoxy, $C_1$–$C_4$-alkoxycarbonyl, di-($C_1$–$C_4$-alkyl)aminocarbonyl, cyano or nitro, a $C_3$–$C_8$-cycloalkyl radical, or a $C_1$–$C_4$-alkylenephenyl, phenyl or naphthyl radical without substitution in the phenyl moiety or with substitution by halogen, $C_1$–$C_3$-alkyl, $C_1$–$C_3$-alkoxy, trifluoromethyl, cyano or nitro.

The meanings mentioned above for substituents $R^2$ and $R^5$ in the formula I are collective terms for individual listings of the individual group members. All hydrocarbon chains, ie. all the alkyl, alkenyl, alkynyl and alkoxy moieties, can be straight-chain or branched. Halogenated substituents preferably carry 1–6 identical or different halogen atoms.

Specific examples of meanings are:
Halogen:
fluorine, chlorine, bromine and iodine, preferably fluorine and chlorine;
$C_1$–$C_3$-alkyl:
methyl, ethyl, n-propyl, 1-methylethyl;
$C_1$–$C_{10}$-alkyl:
$C_1$–$C_3$-alkyl as mentioned above, and n-butyl, 1-methylpropyl, 2-methylpropyl and 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-2-methylpropyl; n-heptyl, n-octyl, n-nonyl, n-decyl, 1-methylhexyl, 1-ethylhexyl, 1-methylheptyl, 1-methyloctyl, 1-methylnonyl;
$C_2$–$C_{10}$-alkenyl:
ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, hept-2-en-1-yl, oct-2-en-1-yl, non-2-en-1-yl, dec-2-en-1-yl, preferably ethenyl and prop-2-en-1-yl;
$C_2$–$C_{10}$-alkynyl:
ethynyl and $C_3$–$C_6$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, hept-2-yn-1-yl, oct-2-yn-1-yl, non-2-yn-1-yl, dec-2-yn-1-yl, preferably prop-2-yn-1-yl, 1-methylprop-2-yn-1-yl;

$C_1$–$C_3$-fluoroalkyl:
  $C_1$–$C_3$-alkyl as mentioned above where in each case 1–5 hydrogen atoms are replaced by fluorine, for example fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoropropyl, preferably difluoromethyl, trifluoromethyl, 2,2,2-trifluoroethyl, pentafluoroethyl, 3,3,3-trifluoropropyl, particularly preferably trifluoromethyl;

$C_1$–$C_{10}$-haloalkyl:
  $C_1$–$C_{10}$-alkyl as mentioned above where in each case 1–6 hydrogen atoms are replaced by fluorine, chlorine and/or bromine, ie. for example chloromethyl, dichloromethyl, trichloromethyl, fluoromethyl, difluoromethyl, trifluoromethyl, chlorofluoromethyl, dichlorofluoromethyl, chlordifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluormethyl;

$C_2$–$C_{10}$-haloalkenyl:
  $C_2$–$C_{10}$-alkenyl as mentioned above where in each case 1–6 hydrogen atoms are replaced by fluorine, chlorine and/or bromine;

$C_2$–$C_{10}$-haloalkynyl:
  $C_2$–$C_{10}$-alkynyl as mentioned above where in each case one to six hydrogen atoms are replaced by fluorine, chlorine and/or bromine;

$C_3$–$C_8$-cycloalkyl:
  cyclopropyl, cyclobutyl, cyclopentyl, cyclohexyl, cycloheptyl and cyclooctyl, preferably cyclopropyl, cyclopentyl and cyclohexyl;

cyano-($C_1$–$C_{10}$)-alkyl:
  $C_1$–$C_{10}$-alkyl as mentioned above where in each case one hydrogen atoms is replaced by the cyano group, ie. for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, and 2-cyanomethylprop-2-yl, 6-cyanohex-1-yl, 7-cyanohept-1-yl, 8-cyanooct-1-yl, 9-cyanonon-1-yl, 10-cyanodec-1-yl; preferably cyanomethyl, 1-cyano-1-methylethyl;

$C_1$–$C_4$-alkoxy and the alkoxy moieties of $C_1$–$C_4$-alkoxycarbonyl:
  methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

di-($C_1$–$C_4$-alkyl)aminocarbonyl:
  N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)-aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl )-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl) aminocarbonyl, preferably dimethylaminocarbonyl and diethylaminocarbonyl;

$C_1$–$C_4$-alkylene:
  methylene, ethylene, propylene, 1-methylethylene, butylene, 1,2-dimethylethylene and 1-ethylethylene;

phenyl without substitution or with substitution by halogen, $C_1$–$C_3$-alkyl, $C_1$–$C_3$-alkoxy, trifluoromethyl, cyano or nitro:
  2-, 3-, 4-chlorophenyl, 2-, 3-, 4-tolyl, 2-chloro-4-methylphenyl, 2,4-dichlorophenyl, 2,4,6-trichlorophenyl, 2,6-dichloro-4-methylphenyl, 2-, 3-, 4-methoxyphenyl, 2-chloro-4-methoxyphenyl, 3-chloro-4-methoxyphenyl, 2-, 3-, 4-trifluoromethylphenyl, 2-, 3-, 4-cyanophenyl, 2-, 3-, 4-nitrophenyl, 2-methyl-4-nitrophenyl, 2-chloro-4-trifluoromethylphenyl, 2-chloro-4-nitrophenyl and unsubstituted phenyl.

Particularly preferably, the novel process is suitable for preparing compounds I in which
n is 1 or 2;
$R^2$ is chlorine or trifluoromethyl;
$R^4$ is fluorine and
$R^5$ is a $C_1$–$C_8$-alkyl, $C_2$–$C_8$-alkenyl or $C_3$–$C_8$-alkynyl radical without substitution or with substitution by halogen or $C_1$–$C_4$-alkoxy, an unsubstituted $C_3$–$C_8$-cycloalkyl radical, or a benzyl or phenyl radical without substitution in the phenyl moiety or with substitution by halogen, $C_1$–$C_3$-alkyl, $C_1$–$C_3$-alkoxy, nitro, cyano or trifluoromethyl;
and especially preferably compounds I in which
n is 2;
$R^2$ is chlorine or trifluoromethyl;
$R^5$ is a $C_1$–CB-alkyl radical without substitution or with substitution by chlorine or methoxy, a benzyl or phenyl radical without substitution in the phenyl moiety or with substitution by chlorine, methyl, methoxy or trifluoromethyl.

The thiopyridines I' according to the invention are useful intermediates for preparing crop protection agents, in particular herbicides from the phenylpyridine class as described in WO-A 95/02580.

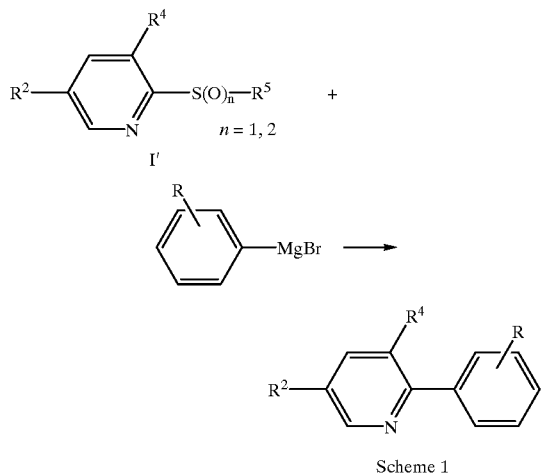

Scheme 1

A particularly advantageous process for preparing herbicidal phenylpyridines based on the sulfoxides Ib and sulfones Ic prepared according to the invention is described in DE Appl. No. 197 226 60.4 and in DE Appl. No. 196 36995.9 (see Scheme 1). Additionally, however, the thiopyridines I' can also be used as intermediates in organic syntheses for preparing inter alia drugs and dyes.

PROCESS EXAMPLES

Preparation of the pyridine thioethers Ia

Example 1

3-Chloro-2-octylthio-5-trifluoromethylpyridine

At 23° C., 17.6 g (0.1166 mol) of n-octanethiol were added with stirring over a period of 5 minutes to a mixture of 25 g (0.1132 mol) of 97.8% pure 2,3-dichloro-5-trifluoromethylpyridine and 7 mg (0.1 mol %) of copper powder, and the mixture was stirred at 185° C. for 4 h. After cooling, the reaction mixture was partitioned between methylene chloride and water and the organic phase was dried and concentrated. 35.4 g (96.1% of theory) of the title compound of $$\frac{24}{n_D}$$

=1.4985 were obtained.

Example 2

3-Chloro-2-benzylthio-5-trifluoromethylpyridine

Example 1 was repeated, except that 14.6 g of 99% pure benzyl mercaptan were stirred with 0.7 mg (0.01 mol %) of copper powder at 180° C. for 4 h. 32.4 g (94.3% of theory) of the title compound of $$\frac{24}{n_D}$$

=1.5645 were obtained.

Example 3

3-Chloro-2-phenylthio-5-trifluoromethylpyridine 26 g (0.233 mol) of 98.7% pure thiophenol, 50 g (0.226 mol) of 97.8% pure 2,3-dichloro-5-trifluoromethylpyridine and 14.7 mg (0.23 mmol) of copper powder were reacted by the method of Example 1, except that the reaction time was only 1 h and the reaction temperature was 160–170° C. The yield was 99%.

Example 4

3-Fluoro-2-phenylthio-5-trifluoromethylpyridine

At 148–156° C., 59.6 g (0.326 mol) of 2,3-difluoro-5-trifluoromethylpyridine were added over a period of 2.5 h to 37.7 g (0.338 mol) of 98.7% pure thiophenol and 2.1 mg (0.01 mol %) of copper powder, and the mixture was stirred at 156–164° C. for 2 hours. After cooling, the residue was taken up in methylene chloride, washed with 0.5 N aqueous sodium hydroxide solution and water, dried over magnesium sulfate and concentrated under reduced pressure. 88.9 g (100% of theory) of the title compound of $$\frac{24}{n_D}$$

=1.5539 were obtained.

Example 5

5-Chloro-3-fluoro-2-phenylthiopyridine

Starting from 93 g (0.508 mol) of 2,3-difluoro-5-chloropyridine, 58.8 g (0.5276 mol) of 98.7% pure thiophenol and 3.2 mg (0.01 mol %) of copper powder which were stirred in a pressure apparatus at 185° C. for 1.5 h and worked up by the method of Example 1, 121.5 g (99.9% of theory) of the title compound were obtained as a colorless oil. 1H-NMR (ppm, $d_6$DMSO) 8.35 (s/1H), 8.05 (d/1H), 7.4–7.6 (m/5H).

Preparation of the sulfoxides Ib and sulfones Ic

Example 6

3-Chloro-2-phenylsulfonyl-5-trifluoromethylpyridine
Variant a: starting from 2,3-dichloro-5-trifluoromethylpyridine At 20–40° C., 26 g (0.233 mol) of 98.7% pure thiophenol were added to a mixture of 50 g (0.226 mol) of 97.8% pure 2,3-dichloro-5-trifluoromethylpyridine and 14.7 mg (0.23 mmol) of copper powder (=0.1%, based on the pyridine) with stirring over a period of 20 min. Over a period of 30 min, the reaction mixture was heated to 170° C. with stirring, vigorous evolution of HCl starting at 120° C. After 40 min of stirring at 160–170° C., the conversion rate was 98.9% according to HPLC.

80 ml of water and 260 ml of glacial acetic acid were then added with stirring to the cooled flask, and a mixture totaling 294 g (0.532 mol) of 13.5% strength sodium hypochlorite and 300 ml of water was added in 4 portions, in each case over a period of 15 min. After each addition, the mixture was stirred at 30° C. with gentle cooling for 15 min, and finally for another 1 h. The reaction mixture was poured into 1.5 l of ice-water and extracted with methylene chloride. The organic phase was washed with water and saturated sodium bicarbonate solution, dried and concentrated. 73 g (100% of theory) of the title compound of mp. 86–87° C. were obtained.

In further experiments, the amount of catalyst (amount of copper) in the first step of the one-pot synthesis was reduced down to 0.01% without any loss in yield. If the amount of catalyst is further reduced to 0.003% of Cu, the reaction time of the thioether synthesis increases to 6 hours and the yield is reduced to 95.1% of isolated sulfone.

Variant b: starting from 3-chloro-2-phenylthio-5-trifluoromethylpyridine

At 25–30° C., 273.2 g (0.495 mol) of a 13.5% strength sodium hypochlorite solution in 240 ml of water were added to a mixture of 65.2 g (0.225 mol) of 3-chloro-2-phenylthio-5-trifluoromethylpyridine in 100 ml of water and 100 ml of glacial acetic acid over a period of 2 h. After 2 h of stirring at 25° C., a further 70 ml of glacial acetic acid were added and 84.5 g (0.153 mol) of 13.5% strength sodium hypochlorite solution were introduced over a period of 30 min. The reaction mixture was stirred at 25° C. for 3 h and then extracted with methylene chloride, and the organic extract was washed with water, saturated sodium bicarbonate solution and once more with water. The extract was subsequently dried over magnesium sulfate and concentrated under reduced pressure. 70.9 g (98% of theory) of the title compound of mp. 91° C. were obtained. According to GC, the purity was 100%.

Example 7
3-Chloro-2-n-propylsulfinyl-5-trifluoromethylpyridine

At 15–20° C., 8.4 g (0.124 mol) of 50% strength hydrogen peroxide were added over a period of 15 min with stirring to a mixture of 31 g (0.1213 mol) of 3-chloro-2-n-propylthio-5-trifluoromethylpyridine in 150 ml of acetic acid, the temperature increasing to 27° C. over a period of 6 h. The reaction mixture was stirred at 25° C. for 14 h and then poured into ice-water and extracted 3 times with methylene chloride. The organic phase was washed with water and saturated sodium bicarbonate solution, dried and concentrated under reduced pressure, giving 32 g (97.2% of theory) of the title compound of mp. 51–53° C.

Example 8
3-Chloro-2-n-propylsulfonyl-5-trifluoromethylpyridine

At 20–25° C., 11.7 g (0.172 mol) of 50% strength hydrogen peroxide were added with stirring over a period of 30 min to 20 g (0.0783 mol) of 3-chloro-2-n-propylthio-5-trifluoromethylpyridine in 150 ml of glacial acetic acid, the temperature increasing to up to 31° C. over a period of 8 h. After 60 h of stirring, the reaction mixture had cooled to 25° C. and was then poured into ice-water and worked up as described. 21 g (93.3% of theory) of the title compound of mp. 41–42° C. were obtained.

Example 9
3-Chloro-2-phenylsulfinyl-5-trifluoromethylpyridine

At 25° C., 11.76 g (0.173 mol) of 50% strength hydrogen peroxide were added over a period of 20 min to a mixture of 50 g (0.173 mol) of 3-chloro-2-phenylthio-5-trifluoromethylpyridine in 50 ml of trifluoroacetic acid and 250 ml of acetic acid. The reaction mixture was stirred at 30–28° C. for 4 h and then extracted with methylene chloride, and the organic phase was washed with sodium bicarbonate solution and water. The organic phase was dried over magnesium sulfate and concentrated under reduced pressure, affording 48.5 g of colorless crystals of mp. 67–68° C. According to NMR analysis, the crystals contained 44.9 g (85% of theory) of the pure title compound and 3.6 g (6.4% of theory) of the corresponding sulfone.

Example 10
3-Fluoro-2-phenylsulfinyl-5-trifluoromethylpyridine 20 g (0.0693 mol) of 95% pure 3-fluoro-2-phenylthio-5-trifluoromethylpyridine were introduced into 100 ml of glacial acetic acid and 20 ml of trifluoroacetic acid and over a period of 5 min, with stirring at 22° C., 5.64 g (0.083 mol) of 50% strength hydrogen peroxide were added. The reaction mixture was stirred at 22° C. for 10 h and then poured into 1 l of ice-water and extracted with methylene chloride. The organic phase was washed with saturated sodium bicarbonate solution and water. After drying, filtration through silica gel and concentration under reduced pressure, 19.1 g (95.4% of theory) of the title compound of $$\overline{n_D^{24}}$$

=1.5522 were obtained.

Example 11
3-Fluoro-2-phenylsulfonyl-5-trifluoromethylpyridine

At 25–30° C., 63.2 g (0.1145 mol) of 13.5% strength sodium hypochlorite were added with stirring in 4 portions, in each case over a period of 10 min, to a mixture of 13.6 g (0.0498 mol) of the compound of Example 5 in 85 ml of water and 60 ml of glacial acetic acid. The reaction mixture was stirred for a total of 2.5 h, poured into 1 l of ice-water and extracted with methylene chloride. The organic phase was washed with saturated sodium bicarbonate solution and water. After drying and concentrating under reduced pressure, 15.1 g (98.9% of theory) of the title compound of mp. 82–83° C. were obtained.

Example 12
5-Chloro-3-fluoro-2-phenylsulfinylpyridine

At 23–28° C., 33.8 g (0.497 mol) of 50% strength hydrogen peroxide were added over a period of 15 min with stirring to a solution of 119 g (0.497 mol) of the compound of Example 6 in 500 ml of glacial acetic acid and 150 ml of trifluoroacetic acid. The reaction mixture was stirred at 23° C. for 14 h, poured into 2 l of ice-water and extracted with methylene chloride. The organic phase was washed with saturated sodium bicarbonate solution and water. After concentration, 123.5 g (97.3% of theory) of the title compound were obtained as colorless crystals. The crystals were stirred with ether/pentane 2:8 and 116.1 g (91.6% of theory) of mp. 77–78° C. remained.

What is claimed is:
1. A process for preparing sulfoxides of the formula Ib or sulfones of the formula Ic

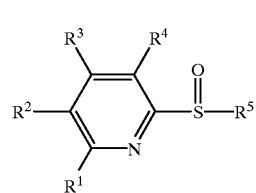

Ib

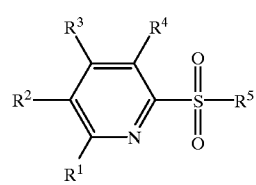

Ic where $R^1, R^2, R^3$ and $R^4$ are identical or different and each is hydrogen, halogen, nitro, cyano, $C_1$–$C_6$-alkyl, $C_2$–$C_6$- alkenyl, $C_2$–$C_6$-alkynyl, $C_1$–$C_6$-alkoxy, $C_2$–$C_6$-alkenyloxy, $C_3$–$C_6$-alkynyloxy, $C_1$–$C_6$-alkylthio, $C_2$–$C_6$-alkenylthio, $C_3$–$C_6$-alkynylthio, $C_1$–$C_6$-alkylsulfinyl, $C_2$–$C_6$-alkenylsulfinyl, $C_3$–$C_6$-alkynylsulfinyl, $C_1$–$C_6$-alkylsulfonyl, $C_2$–$C_6$-alkenylsulfonyl, $C_3$–$C_6$-alkynylsulfonyl, the alkyl, alkenyl and alkynyl moieties of these groups optionally substituted with up to 6 halogen atoms; a $C_1$–$C_4$-alkylenephenyl, phenyl, phenoxy or naphthyl radical wherein the phenyl and naphthyl moieties are unsubstituted or substituted with halogen, $C_1$–$C_3$-alkyl, $C_1$–$C_3$-alkoxy, trifluoromethyl, cyano or nitro; $COOR^6$, $CONR^7R^8$, $SO_2NR^7R^8$ or $COR^6$; the pyridine $R^5$ is an unsubstituted or substituted $C_1$–$C_{10}$-alkyl, $C_2$–$C_{10}$-alkenyl or $C_2$–$C_{10}$-alkynyl radical said substituents being halogen, $C_1$–$C_4$-alkoxy, $C_1$–$C_4$-alkoxycarbonyl, di-($C_1$–$C_4$-alkyl)aminocarbonyl, cyano or nitro, a $C_3$–$C_8$-cycloalkyl radical, a $C_1$–$C_4$-alkylenephenyl, phenyl or naphthyl radical wherein the phenyl and naphthyl moieties are unsubstituted or substituted with halogen, $C_1$–$C_3$-alkyl, $C_1$–$C_3$-alkoxy, trifluoromethyl, cyano or nitro, $R^6$, $R^7$ and $R^8$ are identical or different and each is hydrogen, $C_1$–$C_6$-alkyl, $C_3$–$C_6$-cycloalkyl, $C_2$–$C_6$-alkenyl, $C_3$–$C_6$-alkynyl, optionally these groups are substituted with up to 6 halogen atoms; a phenyl or $C_1$–$C_4$-alkylenephenyl radical wherein the phenyl moiety is unsubstituted or substituted by halogen, $C_1$–$C_3$-alkyl, $C_1$–$C_3$-alkoxy, trifluoromethyl, cyano or nitro, which comprising reacting substituted 2-halopyridines of the formula II

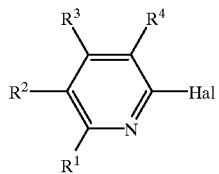

II in which $R^1$, $R^2$, $R^3$ and $R^4$ are each as defined above and Hal is fluorine, chlorine or bromine, in a first step with a thio compound of the formula III

III in which $R^5$ is as defined above, in the presence of a copper catalyst to give initially a pyridine thioether of the formula Ia

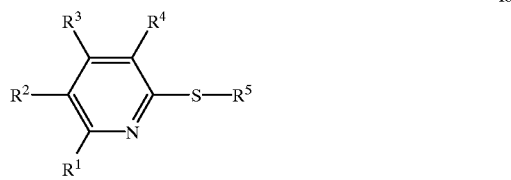

Ib and then oxidizing this stepwise to give the sulfoxide Ib or sulfone Ic.

2. A process as claimed in claim 1, wherein the 2-halopyridines II are reacted with a thio compound of the formula III in the presence of 0.001 to 10 mol % of a copper catalyst.

3. A process as claimed in claim 1 wherein the stepwise oxidation of the pyridine thioethers Ia to the sulfoxides Ib and sulfones Ic is carried out using hydrogen peroxide in a mixture of acetic acid and trifluoroacetic acid in a volume ratio of 6:1 to 4:1.

4. A process as claimed in claim 1, wherein the oxidation of the pyridine thioethers Ia to the sulfones Ic is carried out using hypochlorous acid or its alkali metal salt.

\* \* \* \* \*

UNITED STATES PATENT AND TRADEMARK OFFICE
CERTIFICATE OF CORRECTION

PATENT NO. : 6,191,280 B1  
DATED : February 20, 2001  
INVENTOR(S) : Hamprecht et al.

Page 1 of 1

It is certified that error appears in the above-identified patent and that said Letters Patent is hereby corrected as shown below:

Column 15, claim 1,
Line 13, delete "the pyridine".

Signed and Sealed this

Nineteenth Day of February, 2002

Attest:

JAMES E. ROGAN  
*Director of the United States Patent and Trademark Office*

*Attesting Officer*